United States Patent
Merschaert et al.

(10) Patent No.: US 8,969,620 B2
(45) Date of Patent: Mar. 3, 2015

(54) PROCESS FOR THE PREPARATION OF AMINO ACID DERIVATIVES

(75) Inventors: Alain Merschaert, Brussels (BE); Didier Bouvy, Brussels (BE); David Vasselin, Brussels (BE); Nicolas Carly, Brussels (BE)

(73) Assignee: UCB Pharma GmbH, Monheim (DE)

( * ) Notice: Subject to any disclaimer, the term of this patent is extended or adjusted under 35 U.S.C. 154(b) by 0 days.

(21) Appl. No.: 13/824,044

(22) PCT Filed: Sep. 29, 2011

(86) PCT No.: PCT/EP2011/067038
§ 371 (c)(1),
(2), (4) Date: Mar. 15, 2013

(87) PCT Pub. No.: WO2012/041986
PCT Pub. Date: Apr. 5, 2012

(65) Prior Publication Data
US 2013/0190533 A1    Jul. 25, 2013

(30) Foreign Application Priority Data

Oct. 1, 2010 (EP) .................................. 10012680

(51) Int. Cl.
*C07C 237/22* (2006.01)
*C07C 231/16* (2006.01)
*C07C 231/02* (2006.01)
*C07C 231/12* (2006.01)
*C07C 231/18* (2006.01)

(52) U.S. Cl.
CPC ............ *C07C 231/02* (2013.01); *C07C 231/12* (2013.01); *C07C 231/18* (2013.01); *C07C 237/22* (2013.01); *C07C 231/16* (2013.01); *C07B 2200/07* (2013.01)
USPC ......................................... 564/158; 564/139

(58) Field of Classification Search
CPC ..................................................... C07C 237/22
USPC ................................................ 564/139, 158
See application file for complete search history.

(56) References Cited

U.S. PATENT DOCUMENTS 5,773,475 A    6/1998 Kohn

FOREIGN PATENT DOCUMENTS

WO    2006/037574 A1    4/2006
WO    2010/052011 A1    5/2010

OTHER PUBLICATIONS

Andurkar, S.V. et al., "Synthesis and anticonvulsant activities of (R)-(O)-methylserine derivatives", Tetrahedron Asymmetry, 1998, 9(21), 3841-3854.
Ramer et al., "Mechanism of Formation of Serine Beta-Lactones by Mitsunobu Cyclization: Synthesis and Use of L-Serine Stereospecifically Labelled with Deuterium at C-3", Canadian Journal of Chemistry, 1986, vol. 64, 706-713.
Morieux et al., "Synthesis and anticonvulsant activities of N-benzyl (2R)-2-acetamido-3-oxysubstituted propionamide derivatives", Bioorganic & Medicinal Chemistry, 2008, 16(19), 8968-8975.

*Primary Examiner* — Shailendra Kumar
(74) *Attorney, Agent, or Firm* — McDonnell Boehnen Hulbert & Berghoff LLP

(57) ABSTRACT

The present invention relates to a process of manufacture of compounds of formula (B) wherein $R^1$, $R^2$ and $R^3$ are as defined for compounds of formula (A), which process comprises hydrogenation of compounds of general formula (A). In particular, the present invention relates to an improved process for the manufacture of Lacosamide (LCM), (R)-2-acetamido-N-benzyl-3-methoxypropion-amide (B1), which is useful as an anticonvulsive drug.

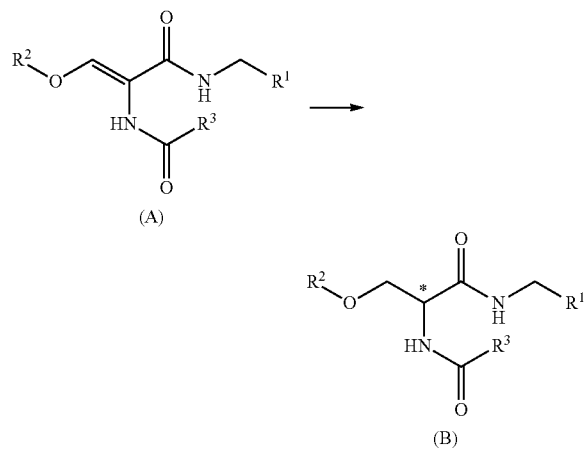

14 Claims, 1 Drawing Sheet

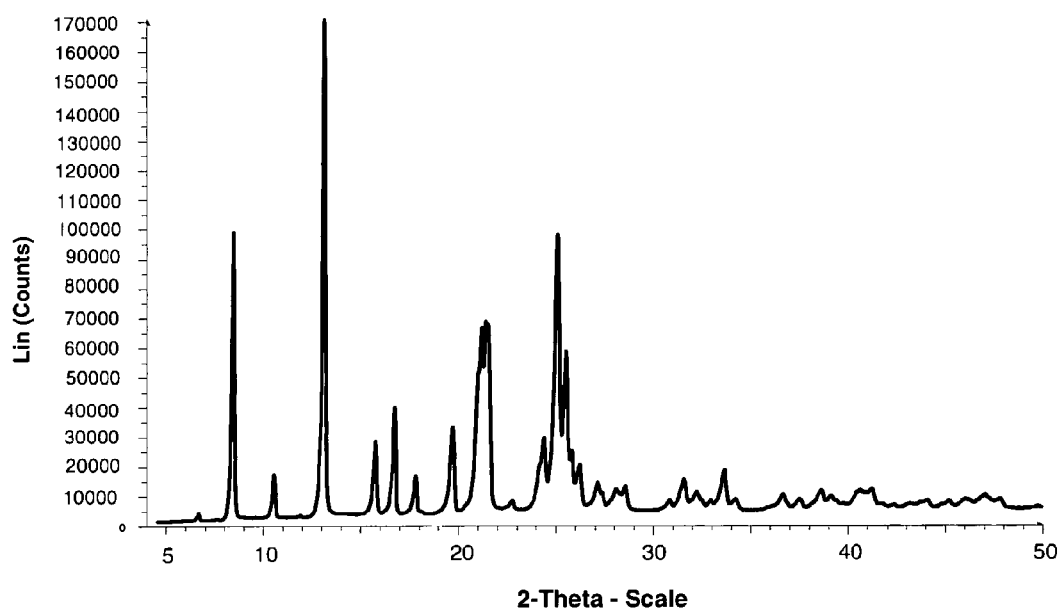
Experimental powder X-ray diffractogram of polymorphic form (I) of Lacosamide

PROCESS FOR THE PREPARATION OF AMINO ACID DERIVATIVES

This application is an U.S. national phase of International Application No. PCT/EP2011/067038 filed on Sep. 29, 2011, which claims priority to European Patent Application No. 10012680.4 filed on Oct. 1, 2010.

The present patent application relates to a novel process for the preparation of amino acid derivatives.

In particular, the present application relates to an improved process for the manufacture of Lacosamide (LCM), (R)-2-acetamido-N-benzyl-3-methoxypropion-amide (B1), which is useful as an anticonvulsive drug.

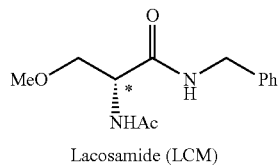 [SMILES: COC[C@@H](NC(C)=O)C(=O)NCc1ccccc1]

Lacosamide (LCM)

LCM has demonstrated antiepileptic effectiveness in different rodent seizure models and antinociceptive potential in experimental animal models that reflect distinct types and symptoms of neuropathic as well as chronic inflammatory pain.

U.S. Pat. No. 5,378,729 describes the preparation of functionalized amino acids by reacting amines with acetylating derivates of a carboxylic acid under amide forming conditions. U.S. Pat. No. 5,378,729 is however silent on the direct preparation of a single enantiomer of functionalized amino acids, such as Lacosamide.

U.S. Pat. No. 5,773,475 relates to methods of preparation of 'substantially optically pure' Lacosamide, as defined therein, starting from D-Serine. Said method of preparation involves the use of methyl iodide and silver (I) oxide as O-methylation agent which presents the disadvantages of being expensive and leads to partial racemization of the product undergoing the O-methylation. This is a main drawback in terms of industrial productivity of the process.

U.S. Pat. No. 6,048,899 describes variants of the process described in U.S. Pat. No. 5,773,475.

International patent application published as WO 2006/037574 relates to an improved synthesis route to Lacosamide wherein an alternative O-methylation agent to methyl iodide and silver (I) oxide is used, in particular dimethylsulphate.

However, the use of an excess of dimethylsulphate as described in WO 2006/037574 may lead to safety or environmental issues when producing Lacosamide on a large scale. Moreover the use of N-protection/N-deprotection steps of the amine moiety may lead to cost and productivity issues for the industrial production of the overall process.

International patent application WO2010/0522011 describes an improved process for the preparation of Lacosamide. However, this process requires the use of chiral separation methods, such as Multiple Column Chromatography (MCC). Hence, for this process to be productive and cost-effective, the use of special equipment and the recycling of the unwanted enantiomer are necessary.

S. V. Andurkar et al. (in Tetrhaedron: Asymmetry 9 (1998) 3841-3854) disclose a process of manufacture of (R)-2-acetamido-N-benzyl-3-methoxypropionamide in an enantiomeric excess of 30%. Such a low enantiomeric excess would require additional chiral separation steps to be performed on (R)-2-acetamido-N-benzyl-3-methoxypropionamide in order to obtain substantially optically pure (R)-2-acetamido-N-benzyl-3-methoxypropion-amide. There is therefore a need to find an alternative and improved process for the manufacture of Lacosamide which would not involve the use of separation methods.

In a first aspect, the present invention provides a compound of general formula (A),

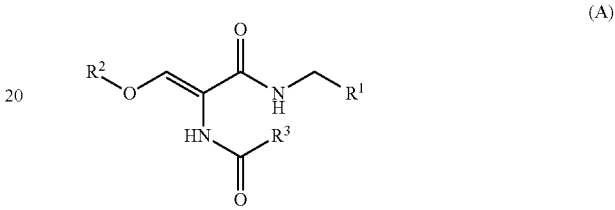

(A)

wherein $R^1$ is an aryl; and $R^2$ and $R^3$ are independently an alkyl.

The term "alkyl", as used herein, is a group which represents saturated, monovalent hydrocarbon radicals having straight (unbranched) or branched moieties, or combinations thereof, and containing 1-10 carbon atoms, preferably 1-10 carbon atoms, more preferably 1-6 carbon atoms; most preferably alkyl groups have 1-4 carbon atoms. Preferred alkyl group is methyl.

"Alkyl" groups according to the present invention may be unsubstituted or substituted.

The term "aryl" as used herein, refers to an unsaturated aromatic carbocyclic group of from 6 to 14 carbon atoms having a single ring (e.g. phenyl) or multiple condensed rings (e.g. naphthyl). Preferred aryl group is phenyl.

Unless otherwise stated reference to the compounds of general formula (A) either individually or collectively are intended to include both Z (Zusammen) and E (Entgegen) isomers and mixtures thereof.

In a particular embodiment, the first aspect of the present invention provides a compound of formula (A) wherein $R^1$ is an aryl and $R^2$ & $R^3$ are the same or different and independently $C_{1-4}$ alkyl.

In a further particular embodiment, the first aspect of the present invention provides a compound of formula (A) wherein $R^1$ is a phenyl and $R^2$ & $R^3$ are independently methyl.

In a more particular embodiment, compound (A) is (Z)-2-acetamido-N-benzyl-3-methoxyacrylamide, herein after referred to as (A1).

Compounds of general formula (A) may be synthetized by reacting compounds of general formula (D) wherein $R^2$ and $R^3$ are as defined for compounds of formula (A) and wherein $R^4$ is hydrogen, herein after referred to as compounds of formula (D'), with a compound of formula $R^1CH_2NH_2$, wherein $R^1$ is as defined for compound of formula (A), in a solvent in the presence of a base, according to following scheme 1.

Scheme 1

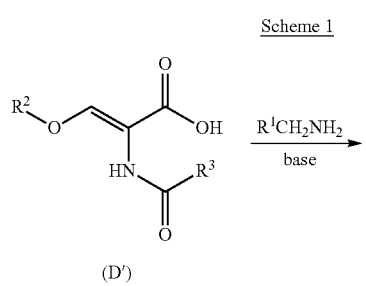

(D')

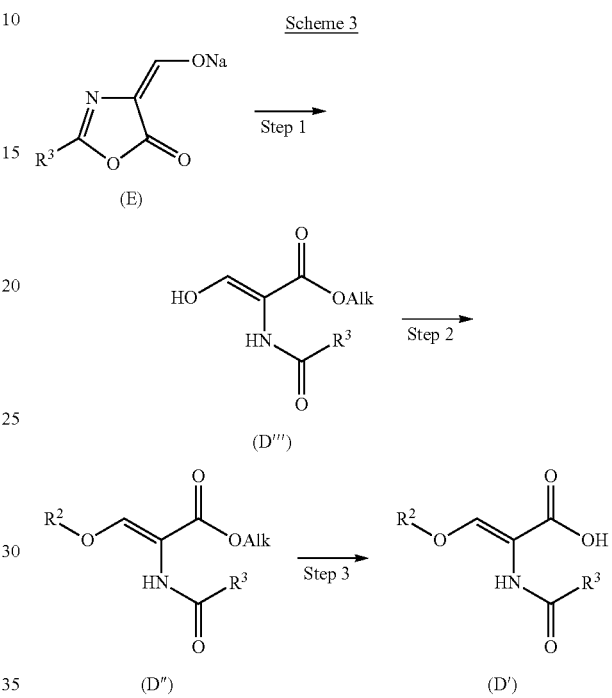

Examples of base that may used for the reaction according to scheme 1 are N-methyl morpholine, triethylamine, alkyl chloroformate such as isobutylchloroformate, ethylchloroformate and methylchloroformate, and aryl chloroformate such as phenylchloroformate.

Examples of solvents according to the present invention are methyl tert-butyl ether (MTBE), dichloromethane, tetrahydrofuran (THF), Me-THF, and ethyl acetate.

In a particular embodiment according to the present invention, compound of formula (D') wherein $R^2$ and $R^3$ are methyl, herein after referred to as (D1), is reacted with benzylamine in methyl tert-butyl ether, dichloromethane, tetrahydrofuran (THF), Me-THF, or ethyl acetate in the presence of isobutyl chloroformate and N-methylmorpholine to afford (Z)-2-acetamido-N-benzyl-3-methoxyacrylamide (A1), as shown in the following scheme 2.

Scheme 2

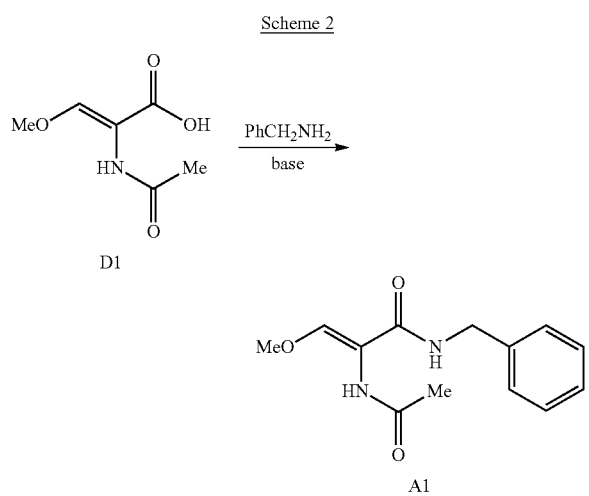

These conditions are particularly advantageous since they allow obtention of compound of formula (A1) exclusively in (Z) form from compound of formula (D1) which is also in (Z) form.

Compound of formula (D') may be obtained according to the following scheme 3 in three steps from compound of formula (E), according to conditions known to the man skilled in the art. $R^2$ and $R^3$ groups in compounds of formula (D'), (D''), (D''') and (E) are as defined for compounds of formula (A).

Step 1 is generally performed in acid conditions. For example, compound (E) may be reacted with acetyl chloride in methanol. Compound of general formula (D''') is generally obtained in (Z) form.

Step 2 is performed in the presence of a base in a solvent. For example, (D''') may be reacted with potassium carbonate in the presence of dimethylsulfate.

Step 3 is generally achieved in the presence of a base in a solvent. Examples of bases that can be used in step 3 are sodium hydroxide, potassium tert-butanolate and potassium carbonate. Examples of solvents that can be used in step 3 are water, tetrahydrofuran, methyl-tert-butyl ether (MTBE) or mixtures thereof.

Compound of general formula (E) may be obtained according to the method described in European Patent application no EP 1 529 778 A1 or according to any other method known to the man skilled in the art.

In a second aspect, the present invention relates to the use of compounds of formula (A) as synthetic intermediates.

In particular, the second aspect of the present invention relates to a process of manufacture of compounds of formula (B) wherein $R^1$, $R^2$ and $R^3$ are as defined for compounds of formula (A), which process comprises hydrogenation of compounds of general formula (A), as shown in the following scheme 4.

Scheme 4

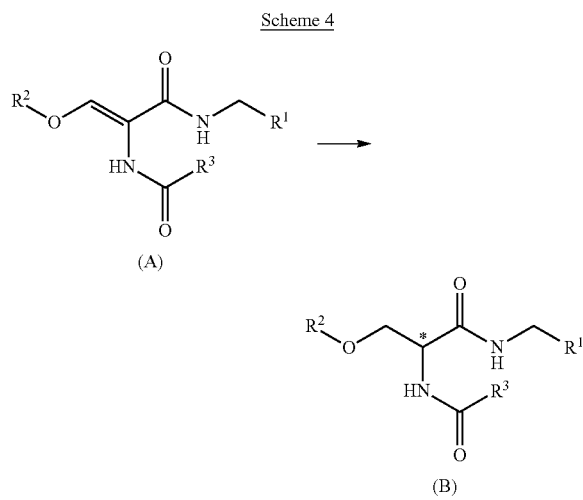

In a particular embodiment of said second aspect, the present invention relates to a process of manufacture of compounds of formula (B), wherein $R^1$, $R^2$ and $R^3$ are as defined for compounds of formula (A), which process comprises catalytic asymmetric hydrogenation of compound of formula (A).

Catalytic asymmetric hydrogenation is described in a great number of books and publications readily available to the man skilled in the art. An example of review article on catalytic asymmetric hydrogenation is William S. Knowles, *Angew. Chem. Int. Ed.*, 2002, 41, 1998-2007

Said catalytic asymmetric hydrogenation is generally performed in the presence of a chiral catalyst.

The chiral catalyst according to the present invention is generally based on rhodium(I) or ruthenium (II).

Preferably the chiral catalyst according to the present invention is based on rhodium(I) complexed by a chiral chelating agent.

There is a great number of chiral chelating agents available commercially or described in the literature. Generally, the chiral chelating agent according to the present invention comprises a phosphine ligand.

(Bis)Phosphine ligands are often difficult to prepare because they possess two chiral centers, which adds to their cost. Furthermore, asymmetric hydrogenation requires the use of special equipment capable of handling $H_2$, which adds to capital costs.

Therefore, there is a need to develop a process which make the large scale production of aminotetralins eco-friendly, safe and yet economically feasible. Present invention bridges this gap and discloses the novel process, which is environmental friendly as well as eliminates the use of costly chiral ligands or auxiliary, column chromatography and suitable for industrial scale up.

A number of catalysts for catalytic asymmetric hydrogenation comprising phosphine ligands have been described in the literature. An example of review article dedicated to chiral phosphorus ligands is W. Tang & X. Zhang, *Chem. Rev.* 2003, 103, 3029-3069. It has further been observed on an industrial scale that the catalyst systems frequently tend to become deactivated depending on the catalyst precursor, the substrate and the ligands. It has further been found that not all catalyst systems that are known in the art enable a complete conversion of the starting materials into the target product with a high enantiomeric selectivity. Thus, there is a continuous need in the art for a process that enables an enantioselective hydrogenation of imines with a high conversion as well as a high enantiomeric excess of the target product wherein the catalyst system is cost effective.

Although a lot of information on catalytic asymmetric hydrogenation is available in the art, finding, for a given substrate, the appropriate catalyst and reaction conditions to obtain the desired product with a high enantioselectivity requires a great amount of experimental work. Furtheron, despite the inherent advantages in using asymmetric catalysis to produce single-enantiomer molecules, the process is not readily amenable to use at an industrial scale because of a number of factors: such as the ready availability of the chiral catalyst for public or licensed use in the required quantity at an affordable price, the presence of impurities in the catalyst, which can either inhibit the effectiveness of the catalyst itself or get carried into the final product where they are difficult to remove and that, there is no single ligand family, much less an individual member of a family, which leads to high enantiomer selectivity with all substrates.

Examples of phosphine ligands which may be used according to the present invention are (R)-(+)-2,2'-bis(diphenylphosphino)-1,1'-binaphthyl((R)-BINAP), (−)-1,2-Bis((2R,5R)-2,5-dimethylphospholano)benzene ((R,R)-Me-DuPhos), (3S,3'S,4S,4'S,11bS,11bS)-(+)-4,4'-Di-t-butyl-4,4',5,5'-tetrahydro-3,3'-bi-3H-dinaphtho[2,1-c:1',2'-e]phosphepin ((S)-BINAPINE), (+)-1,2-Bis(2S,5S)-2,5-diphenylphospholano)ethane ((S,S)-Ph-BPE), (−)-1,2-Bis(2S,5S)-2,5-dimethylphospholano)ethane ((S,S)-Ph-BPE) (R)-(+)-5,5'-Bis(diphenylphosphino)-4,4'-bi-1,3-benzodioxole (SEGPHOS), [4(R)-(4,4'-bi-1,3-benzodioxole)-5,5'-diyl]bis[diphenylphosphine], (R,R)-1,2-Bis[(R)-4,5-dihydro-3H-binaphtho(1,2-c:2',1'-e)phosphepino]benzene (BINAPHANE), (R)-1,13-Bis(diphenylphosphino)-7,8-dihydro-6H-dibenzo[f,h][1,5]dioxonin (TUNEPHOS), (1S,1S1,2R,2R)-(+)-1,1-Di-tert-butyl-[2,2]-diphospholane (TANGPHOS), (1S,2S)-Bis(2-methoxyphenyl) phenylphosphino)ethane((S,S)-DIPAMP)), (−)-2,3-Bis[(2R,5R)-2,5-dimethylphospholanyl]-1-methyl-1H-pyrrole-2,5-dione (catASium® MN(R)), (1R,1R',2S,2S')-(+)-2,2'-Di-t-butyl-2,3,2',3'-tetrahydro-1,1'-bi-1H-isophosphindole ((R,R,S,S)-DUANPHOS) some of which are shown hereafter.

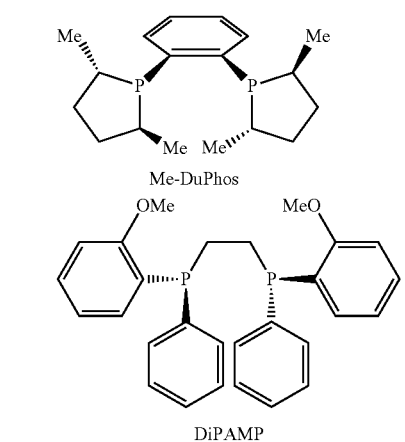

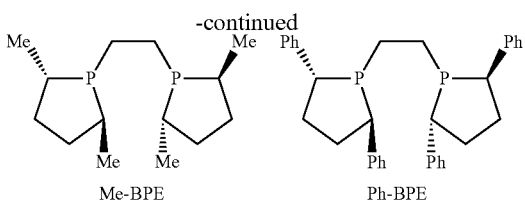

Me-BPE    Ph-BPE

In a particular embodiment according to the present invention, the chiral chelating agent comprises substantially optically pure phosphine ligands, i.e. phosphine ligands in which at least about 95%, preferably at least about 96%, more preferably at least about 97%, most preferably at least about 98%, even most preferably at least about 99% of the compound has the stereogenic center or stereogenic centres in a given configuration (R) or (S).

Generally the phosphine ligand forms a complex with the metal, e.g. ruthenium (II) and is associated to a counterion or to an olefin. Said complex acts as the catalyst to perform the reaction.

Examples of counterions which may be used according to the invention are tetrafluoroborate, perchlorate or trifluorometahnesulfonate. Preferred counterion is tetrafluoroborate.

Examples of olefins that may be associated to the complex according to the present invention are ethylene, 1,3-butadiene, benzene, cyclohexadiene, norbornadiene and cycloocta-1,5-diene.

The catalyst resulting from the association of the metal, phosphine ligand and associated counterion and/or olefin may be pre-formed or generated in situ in the reaction media.

Examples of chiral catalyst which may be used according to the present invention are:1,2-Bis((2R,5R)-2,5-dimethylphospholano)benzene(1,5-cyclooctadiene)rhodium(I) tetrafluoroborate ((R,R)-Me-DuPhos-Rh:(−)); (+)-1,2-Bis((2S,5S)-2,5-diphenylphospholano)ethane(1,5-cyclooctadiene) rhodium(I) tetrafluoroborate ((S,S)-Ph-BPE-Rh); (−)-1,2-Bis ((2S,5S)-2,5-dimethylphospholano)ethane(1,5-cyclooctadiene)rhodium(I) tetrafluoroborate ((S,S)-Me-BPE-Rh); (1S,2S)-Bis(2-methoxyphenyl) phenylphosphino) ethane(1,5-cyclooctadiene)rhodium(I) tetrafluoroborate ((S,S)-DiPAMP-Rh); (1S,1'S,2R,2'R)-1,1-Di-t-butyl-[2,2]-diphospholane (1,5-cyclooctadiene)rhodium(I) tetrafluoroborate ((S,S,R,R)-TANGPHOS-Rh); (R)-(+)-(2,2'-Bis(diphenylphosphino)-1,1'-binaphthyl)ruthenium ((R)-BINAP-Ru); (−)-2,3-Bis[(2R,5R)-2,5-dimethylphospholanyl]-1-methyl-1H-pyrrole-2,5-dione(1,5-cyclooctadiene) rhodium(I) tetrafluoroborate (catASium® MN(R)Rh); (1R, 1R',2S,2S)-(+)-2,2'-Di-t-butyl-2,3,2',3'-tetrahydro-1,1'-bi-1H-isophosphindole(1,5-cyclooctadiene)rhodium(I) tetrafluoroborate ((R, R,S,S)-DUANPHOS-Rh); (R)-(−)-1, 13-Bis(diphenylphosphino)-7,8-dihydro-6H-dibenzo[f,h][1, 5]dioxonin(1,5-cyclooctadiene)rhodium(I) tetrafluoroborate ((R)—C₃-TUNEPHOS-Rh); (R,R)-(−)-1,2-Bis[(R)-4,5-dihydro-3H-binaphtho[1,2-c:2',1'-e]phosphepino]benzene(1, 5-cyclooctadiene)rhodium(I) tetrafluoroborate ((R)-BINAPHANE-Rh); (−)-1,2-Bis((2R,5R)-2,5-diethylphospholano)benzene(1,5-cyclooctadiene)rhodium (I) tetrafluoroborate ((R,R)-Et-DuPhos-Rh).

Said catalytic asymmetric hydrogenation is generally performed in the presence of a solvent. Examples of solvents according to the present invention are methanol, tetrahydrofuran, ethanol and 2-methyl-tetrahydrofuran.

Said catalytic asymmetric hydrogenation is generally performed at a temperature comprised between about 20° C. and about 45° C.

Said catalytic asymmetric hydrogenation is generally performed under pressure of hydrogen in an appropriate vessel. Generally, the pressure of hydrogen is comprised between about 2 barg and about 40 barg. Preferably the pressure of hydrogen is between about 5 barg and about 10 barg.

"Barg" as herein defined represents the unity for the measured pressure with reference to atmospheric pressure i.e. pressure (Barg)=measure pressure (Bar)—atmospheric pressure (Bar).

The ratio substrate/catalyst expressed in Mol % is generally at least about 1000. Preferably, said ratio is at least about 4000.

The process according to the present invention comprising catalytic asymmetric hydrogenation of compounds of formula (A), generally provides optically enriched compounds of formula (B).

The term "optically enriched" as used herein when referring to a particular compound means that more than about 50%, preferably more than about 75%, more preferably more than about 85%, most preferably more than about 94% of the compound has the stereogenic center indicated by (*) in a given configuration (R) or (S).

In a preferred embodiment said process comprising catalytic asymmetric hydrogenation of compounds of formula (A) in the presence of chiral catalyst provides substantially optically pure compounds of formula (B).

The term "substantially optically pure" as used herein when referring to a particular compound means that at least about 95%, preferably at least about 96%, more preferably at least about 97%, most preferably at least about 98%, even most preferably at least about 99% of the compound has the stereogenic center indicated by (*) in a given configuration (R) or (S).

Preferably, the process according to said second aspect of the present invention relates to the manufacture of compounds of formula (B) wherein $R^1$ is an aryl and $R^2$ & $R^3$ are the same or different and independently a $C_{1-4}$ alkyl.

Generally, the catalytic asymmetric hydrogenation according to the present invention provides compounds of formula (B) in conversion rates that are greater than about 90%, preferably greater than about 95%, more preferably greater than about 99%.

In a particular embodiment, the present invention relates to a process of manufacture of optically enriched (R)-2-acetamido-N-benzyl-3-methoxypropion-amide comprising catalytic asymmetric hydrogenation of (Z)-2-acetamido-N-benzyl-3-methoxyacrylamide.

The expression "optically enriched (R)-2-acetamido-N-benzyl-3-methoxypropion-amide" means that more than about 50%, preferably more than about 75%, more preferably more than about 85%, most preferably more than about 94% of the compound has the stereogenic center indicated by (*) in configuration (R).

In a further particular embodiment the present invention relates to a process of manufacture of substantially optically pure (R)-2-acetamido-N-benzyl-3-methoxypropion-amide, herein after referred to as (B1), which process comprises catalytic asymmetric hydrogenation of (Z)-2-acetamido-N-benzyl-3-methoxyacrylamide (A1), as shown in following scheme 5.

Scheme 5

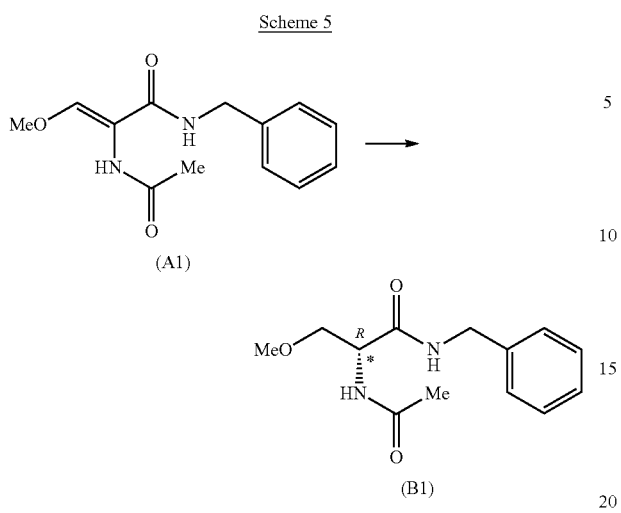

Scheme 6

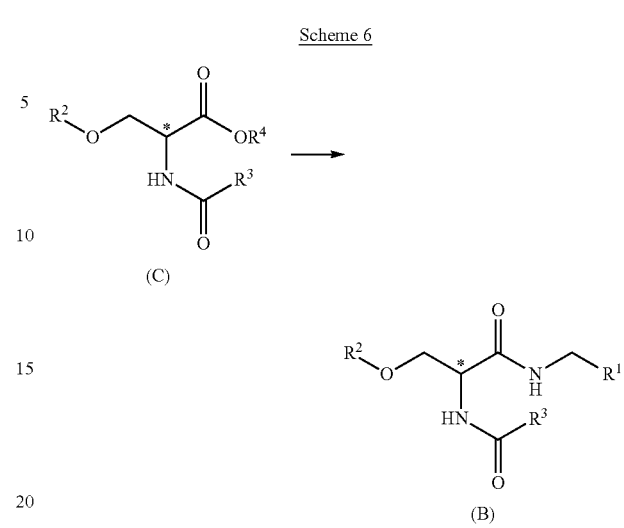

The expression "substantially optically pure (R)-2-acetamido-N-benzyl-3-methoxypropion-amide" means that at least about 95%, preferably at least about 96%, more preferably at least about 97%, most preferably at least about 98%, even most preferably at least about 99% of the compound has the stereogenic center indicated by (*) in configuration (R).

Obtaining compound of formula (B1) as substantially optically pure compound is a particularly surprising result as there are scarce reports in the art of catalytic asymmetric hydrogenation performed on 3-oxy-2-acetamido acrylates, such as (B1), and none in which said catalytic asymmetric hydrogenation is performed with a good enantioselectivity.

In a particular embodiment according to the present invention the desired enantiomer of (B) is obtained with an enantiomeric excess of at least about 90%, preferably at least about 94%, more preferably of at least about 98%. The term "enantiomeric excess" as used herein refers to the amount of an enantiomer with respect to another. It can be calculated as follows:

% $ee = [([A]-[B]):([A]+[B])] \times 100$, where [A] is the concentration of one of the enantiomers, and [B] is the concentration of the other enantiomer. In a completely resolved material, the enantiomeric excess is equal in weight to the total material so that % ee is 100%. In this case the optical purity of the compound will be 100%. The concentration of each of the enantiomers is, of course, expressed on the same basis, and can be expressed on either a weight of molar basis because the enantiomers have the same molecular weight.

In a particular embodiment according to the present invention, the process of manufacture of substantially optically pure compound of formula (B1) comprises catalytic asymmetric hydrogenation of (Z)-2-acetamido-N-benzyl-3-methoxyacrylamide (A1), in the presence of hydrogen at a pressure of 5 barg in methanol and using (+)-1,2-Bis((2S,5S)-2,5-diphenylphospholano)ethane(1,5-cyclooctadiene)rhodium (I) tetrafluoroborate as chiral catalyst.

Alternatively, compounds of formula (B) may be obtained in one or more steps from compounds of general formula (C) wherein $R^2$ and $R^3$ are as defined for compound of formula (A) and wherein $R^4$ is hydrogen or alkyl as shown in the following scheme 6.

When $R^4$ is hydrogen, compounds of formula (B) may be obtained by reacting compounds of general formula (C) with a compound of formula $R^1CH_2NH_2$, in the presence of a base in a solvent.

Examples of solvents that may be used in the reaction according to scheme 6 are THF, 2-Me-THF, dichloromethane, ethylacetate and toluene.

Examples of bases that may be used in the reaction according to scheme 6 are N-methyl morpholine and triethylamine.

In a particular embodiment according to this aspect of the invention, compound of formula (B1) is obtained by reacting N-acetyl-O-methyl-D-serine, herein after referred to as (C1), with benzylamine in THF or dichloromethane in the presence of ethyl chloroformate or isobutylchloroformate as activating agent and N-methylmorpholine as base, according to the following scheme 7.

Scheme 7

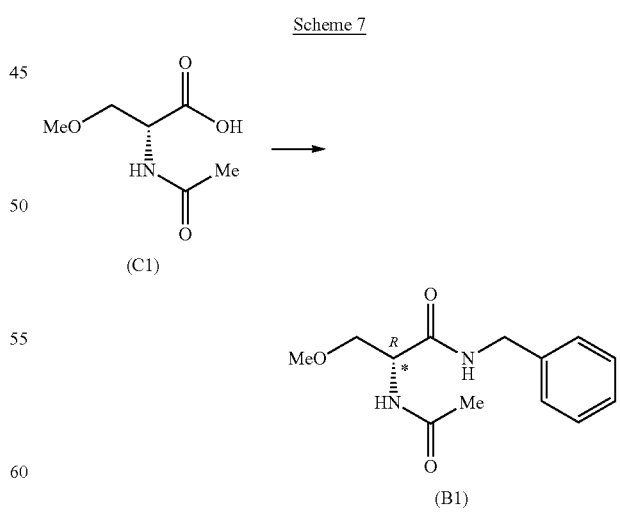

Compounds of formula (C) may be obtained by catalytic asymmetric hydrogenation of compounds of formula (D) wherein $R^2$, $R^3$ and $R^4$ are as defined for compounds of formula (C), as shown in the following scheme 8.

Scheme 8

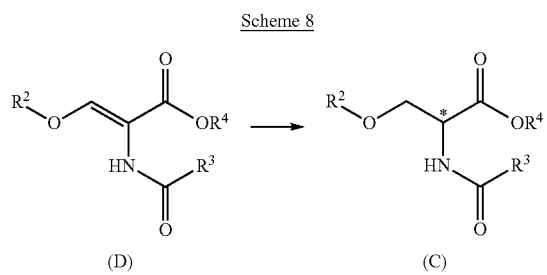

General conditions mentioned here above for the catalytic asymmetric hydrogenation of compounds of formula (A) into compounds of formula (B) may also be applied to the catalytic asymmetric hydrogenation of compounds of formula (D) into compounds of formula (C).

In a preferred embodiment according to this aspect, the present invention relates to a process of manufacture of substantially optically pure compounds of formula (C) comprising catalytic asymmetric hydrogenation of compounds of formula (D) in the presence of a chiral catalyst.

S. E. Ramer et al. (in Canadian Journal of Chemistry, vol. 64, 1986, pp. 706-713), describe the deuteration of a compound of formula (D), in particular (D1). Such deuteration is not performed under asymmetric conditions thereby requiring further separation steps in order to obtain the deuteriated form of compound (C).

In one embodiment, the present invention relates to a process of manufacture of substantially optically pure compounds of formula (C) wherein $R^4$ is hydrogen and $R^2$ & $R^3$ are as defined here above, herein after referred to as compounds of formula (C'), comprising catalytic asymmetric hydrogenation of a compound of formula (D'), as shown in following scheme 9.

Scheme 9

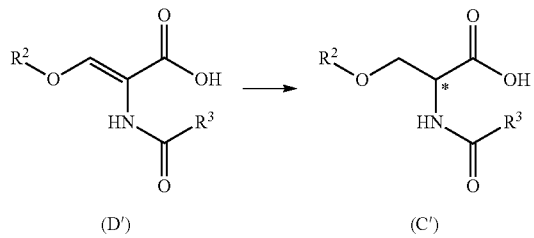

Particularly, according to this aspect, the present invention relates to a process of manufacture of N-acetyl-O-methyl-D-serine, herein after referred to as (C1) comprising catalytic asymmetric hydrogenation of (Z)-2-acetylamino-3-methoxy-2-propenoic acid (D1) as shown in the following scheme 10.

Scheme 10

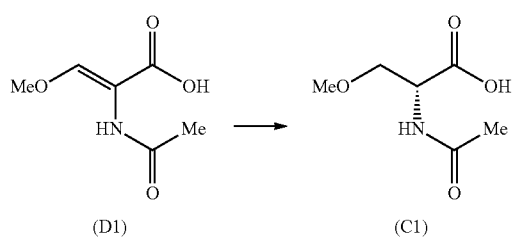

Examples of chiral catalyst which may be used according to this aspect of the invention are 1,2-Bis((2R,5R)-2,5-dimethylphospholano)benzene(1,5-cyclooctadiene)rhodium(I) tetrafluoroborate ((R,R)-Me-DuPhos-Rh:(−)); (+)-1,2-Bis((2S,5S)-2,5-diphenylphospholano)ethane(1,5-cyclooctadiene)rhodium(I) tetrafluoroborate ((S,S)-Ph-BPE-Rh); (−)-1,2-Bis((2S,5S)-2,5-dimethylphospholano)ethane(1,5-cyclooctadiene)rhodium(I) tetrafluoroborate ((S,S)-Me-BPE-Rh); :(1S,2S)-Bis(2-methoxyphenyl)phenylphosphino)ethane(1,5-cyclooctadiene)rhodium(I) tetrafluoroborate ((S,S)-DiPAMP-Rh); (1S,1'S,2R,2'R)-1,1-Di-t-butyl-[2,2]-diphospholane (1,5-cyclooctadiene)rhodium(I) tetrafluoroborate ((S,S,R,R)-TANGPHOS-Rh); (R)-(+)-(2,2'-Bis(diphenylphosphino)-1,1'-binaphthyl)ruthenium ((R)-BINAP-Ru); (+2,3-Bis[(2R,5R)-2,5-dimethylphospholanyl]-1-methyl-1H-pyrrole-2,5-dione(1,5-cyclooctadiene) rhodium(I) tetrafluoroborate (catASium® MN(R)Rh); (1R,1R',2S,2S')-(+)-2,2'-Di-t-butyl-2,3,2',3'-tetrahydro-1,1'-bi-1H-isophosphindole(1,5-cyclooctadiene)rhodium(I) tetrafluoroborate ((R,R,S,S)-DUANPHOS-Rh); (R)-(−)-1,13-Bis(diphenylphosphino)-7,8-dihydro-6H-dibenzo[f,h][1,5]dioxonin(1,5-cyclooctadiene)rhodium(I) tetrafluoroborate ((R)—$C_3$-TUNEPHOS-Rh); (R,R)-(−)-1,2-Bis[(R)-4,5-dihydro-3H-binaphtho[1,2-c:2',1'-e]phosphepino]benzene(1,5-cyclooctadiene)rhodium(I) tetrafluoroborate ((R)-BINAPHANE-Rh); (−)-1,2-Bis((2R,5R)-2,5-diethylphospholano)benzene(1,5-cyclooctadiene)rhodium (I) tetrafluoroborate ((R,R)-Et-DuPhos-Rh).

In a particular embodiment according to this aspect, (+)-1,2-Bis((2S,5S)-2,5-diphenylphospholano)ethane(1,5-cyclooctadiene)rhodium(I) tetrafluoroborate is used as chiral catalyst.

Said catalytic asymmetric hydrogenation is generally performed in the presence of a solvent. Examples of solvents according to the present invention are methanol, THF, and ethanol.

Said catalytic asymmetric hydrogenation is generally performed at a temperature comprised between about 20° C. and about 45° C. Preferably said hydrogenation is performed at room temperature.

Said catalytic asymmetric hydrogenation is generally performed under pressure of hydrogen in an appropriate vessel. Generally, the pressure of hydrogen is comprised between about 2 barg and about 20 barg. Preferably the pressure of hydrogen is comprised between about 5 and about 10 barg.

The ratio substrate/catalyst expressed in Mol % is generally at least about 1000. Preferably, said ratio is at least about 4000.

The N-acetyl-O-methyl-D-Serine (C1) obtained as a result of the process in scheme 10 may be further reacted with benzylamine in THF or dichloromethane in the presence of ethyl chloroformate or isobutylchloroformate as activating agent and N-methylmorpholine as base, to afford substantially optically pure (R)-2-acetamido-N-benzyl-3-methoxypropion-amide (B1) as shown here above in Scheme 7.

In another embodiment, compounds of formula (C') may be obtained by hydrolysis of substantially optically pure compounds of formula (C) wherein $R^4$ is an alkyl, hereafter referred to as compounds of formula (C"), as shown in the following Scheme 11.

Scheme 11

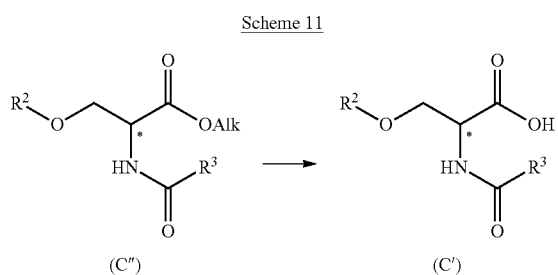

(C″)   (C′)

In a particular embodiment according to the reaction of scheme 11, the present invention relates to a process of manufacture of N-acetyl-O-methyl-D-Serine (C1) by hydrolysis of methyl(R)-2-acetamido-3-methoxypropionate (C2), according to the following scheme 12.

Scheme 12

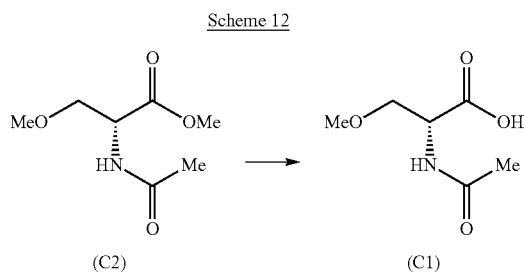 [SMILES: COC[C@@H](NC(C)=O)C(=O)OC ; COC[C@@H](NC(C)=O)C(=O)O ; "(C2)" ; "(C1)"]

(C2)   (C1)

Said hydrolysis is typically performed in the presence of a base such as sodium bicarbonate and in a solvent such as THF or a mixture of THF and water.

The N-acetyl-O-methyl-D-Serine (C1) obtained as a result of the process in scheme 12 may be further reacted with benzylamine in THF or dichloromethane in the presence of ethyl chloroformate or isobutylchloroformate as activating agent and N-methylmorpholine as base, to afford substantially optically pure (R)-2-acetamido-N-benzyl-3-methoxypropion-amide (B1) as shown here above in Scheme 7.

Substantially optically pure compounds of formula (C″) may be obtained by catalytic asymmetric hydrogenation of substantially optically pure compounds of formula (D″).

Hence, in another embodiment, the present invention relates to a process of manufacture of substantially optically pure compounds of formula (C″) comprising catalytic asymmetric hydrogenation of compounds of formula (D″) as shown in the following scheme 13.

Scheme 13

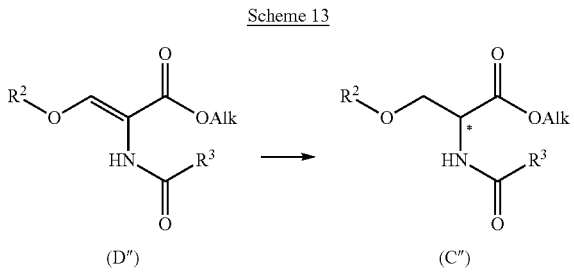

(D″)   (C″)

Said process is performed in the presences of a chiral catalyst. Examples of chiral catalyst which may be used according to this aspect of the invention are 1,2-Bis((2R,5R)-2,5-dimethylpholano)benzene(1,5-cyclooctadiene) rhodium(I) tetrafluoroborate ((R,R)-Me-DuPhos-Rh:(−)); (+)-1,2-Bis((2S,5S)-2,5-diphenylphospholano)ethane(1,5-cyclooctadiene)rhodium(I) tetrafluoroborate ((S,S)-Ph-BPE-Rh); (−)-1,2-Bis((2S,5S)-2,5-dimethylphospholano)ethane (1,5-cyclooctadiene)rhodium(I) tetrafluoroborate ((S,S)-Me-BPE-Rh); (1S,2S)-Bis(2-methoxyphenyl) phenylphosphino) ethane(1,5-cyclooctadiene)rhodium(I) tetrafluoroborate ((S,S)-DiPAMP-Rh); (1S,1′S,2R,2′R)-1,1-Di-t-butyl-[2,2]-diphospholane (1,5-cyclooctadiene)rhodium(I) tetrafluoroborate ((S,S,R,R)-TANGPHOS-Rh); (R)-(+)-(2,2′-Bis(diphenylphosphino)-1,1′-binaphthyl)ruthenium ((R)-BINAP-Ru); (−)-2,3-Bis[(2R,5R)-2,5-dimethylphospholanyl]-1-methyl-1H-pyrrole-2,5-dione(1,5-cyclooctadiene) rhodium(I) tetrafluoroborate (catASium® MN(R)Rh); (1R,1R′,2S,2S)-(+)-2,2′-Di-t-butyl-2,3,2′,3′-tetrahydro-1,1′-bi-1H-isophosphindole(1,5-cyclooctadiene)rhodium(I) tetrafluoroborate ((R,R,S,S)-DUANPHOS-Rh); (R)-(−)-1,13-Bis(diphenylphosphino)-7,8-dihydro-6H-dibenzo[f,h][1,5]dioxonin(1,5-cyclooctadiene)rhodium(I) tetrafluoroborate ((R)—C$_3$-TUNEPHOS-Rh); (R,R)-(−)-1,2-Bis[(R)-4,5-dihydro-3H-binaphtho[1,2-c:2′,1′-e]phosphepino]benzene(1,5-cyclooctadiene)rhodium(I) tetrafluoroborate ((R)-BINAPHANE-Rh); (−)-1,2-Bis((2R,5R)-2,5-diethylphospholano)benzene(1,5-cyclooctadiene)rhodium (I) tetrafluoroborate ((R,R)-Et-DuPhos-Rh).

In a particular aspect according to this embodiment, (1S,2S)-Bis(2-methoxyphenyl) phenylphosphino)ethane(1,5-cyclooctadiene)rhodium(I) tetrafluoroborate ((S,S)-DiPAMP-Rh) is used as chiral catalyst.

Said catalytic asymmetric hydrogenation is generally performed in the presence of a solvent. Examples of solvents according to the present invention are methanol and tetrahydrofuran.

Said catalytic asymmetric hydrogenation is generally performed at a temperature comprised between about 20° C. and about 45° C.

Said catalytic asymmetric hydrogenation is generally performed under pressure of hydrogen in an appropriate vessel. Generally, the pressure of hydrogen is comprised between about 2 barg and about 20 barg. Preferably the pressure of hydrogen is comprised between about 5 and about 10 barg.

The ratio substrate/catalyst expressed in Mol % is generally at least about 1000. Preferably, said ratio is at least about 4000.

In a particular embodiment, the present invention relates to the catalytic asymmetric hydrogenation of (Z)-methyl-2-acetamido-3-methoxypropenoate (D2) into Methyl(R)-2-acetamido-3-methoxypropionate (C2), as shown in the following scheme 14.

Scheme 14

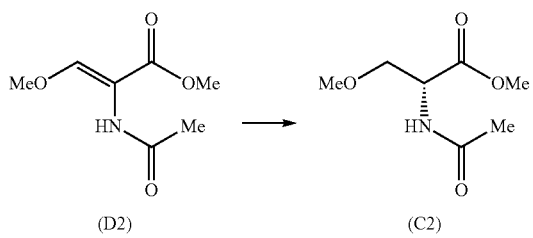

(D2)   (C2)

In a particular embodiment, the present invention relates to a process for the manufacture of substantially optically pure (R)-2-acetamido-N-benzyl-3-methoxypropion-amide (B1) according to claim 12, comprising the following steps:

(i) hydrolysis of (Z)-methyl-2-acetamido-3-methoxypropenoate (D2), into Z-2-acetamido-3-methoxyacryic acid (D1);

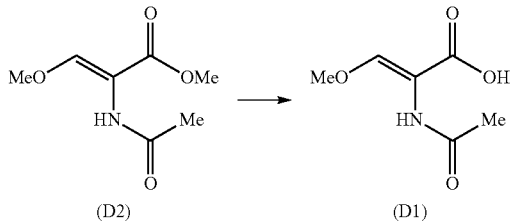 [SMILES: CO/C=C(\NC(C)=O)C(=O)OC ; CO/C=C(\NC(C)=O)C(=O)O ; "(D2)" ; "(D1)"]

(D2)    (D1)

(ii) reacting 2-acetamido-3-methoxyacrylic acid (D1) obtained in step (i) with benzylamine in the presence of ethylchloroformiate (ECF) or isobutylchloroformiate (IBCF) and a base to afford (Z)-2-acetamido-N-benzyl-3-methoxyacrylamide (A1)

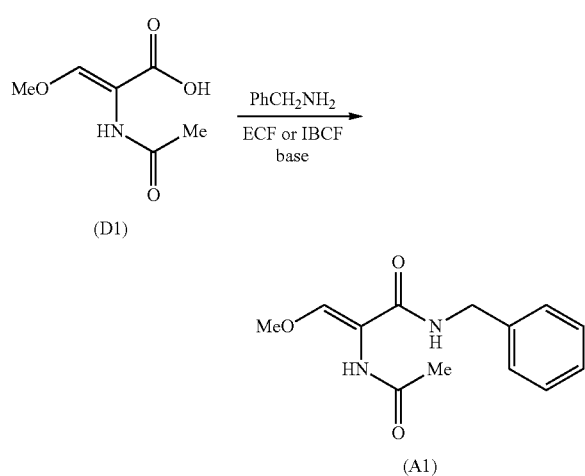

(iii) Performing catalytic asymmetric hydrogenation of (Z)-2-acetamido-N-benzyl-3-methoxyacrylamide (A1) obtained in step (ii), in the presence of a chiral catalyst selected from the group consisting of 1,2-Bis((2R,5R)-2,5-dimethylphospholano)benzene(1,5-cyclooctadiene)rhodium(I) tetrafluoroborate, (+)-1,2-Bis((2S,5S)-2,5-diphenylphospholano)ethane(1,5-cyclooctadiene)rhodium(I) tetrafluoroborate and (−)-1,2-Bis((2S,5S)-2,5-dimethylphospholano)ethane(1,5-cyclooctadiene)rhodium(I) tetrafluoroborate.

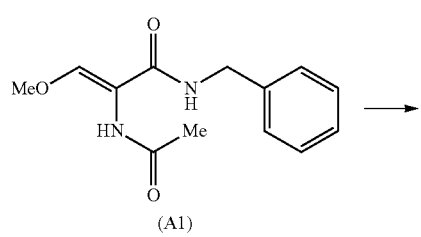

(A1)

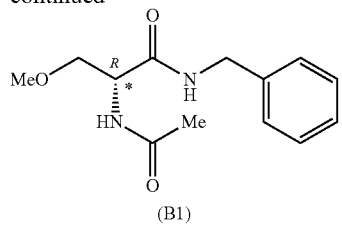

(B1)

Step (i) according to this aspect of the invention is generally performed in the presence of water and a base, preferably potassium tert-butanolate, in a solvent, preferably, methyl tert-butyl ether.

Step (ii) according to this aspect of the invention is generally performed in the presence of benzylamine, isobutylchloroformiate and N-methylmorpholine.

Step (iii) according to this aspect of the invention is generally performed in methanol at a pressure comprised between about 5 and about 10 barg. Preferred chiral catalyst is (+)-1,2-Bis((2S,5S)-2,5-diphenylphospholano)ethane(1,5-cyclooctadiene)rhodium(I) tetrafluoroborate ((S,S)-Ph-BPE))

Substantially optically pure (R)-2-acetamido-N-benzyl-3-methoxypropionamide (B1) may be further crystallized or reslurried in order to achieve desired optical purity.

Substantially optically pure (R)-2-acetamido-N-benzyl-3-methoxypropionamide exists under different crystalline forms of which polymorphic form (I) and polymorphic form (II) are the most commonly encountered.

Polymorphic form (I) is characterized by a powder X-ray diffractogram (FIG. 1) comprising peaks at 8.40, 10.52, 13.06, 15.72, 16.75, 17.8, 19.68, 21.15, 21.37, 24.37, 25.04 and 25.49±0.25 (°2θ), measured with a Cu—Kα irradiation.

In particular, polymorphic form (I) of (R)-2-acetamido-N-benzyl-3-methoxypropionamide is characterized by at least one of the following powder X-ray diffraction peaks: 8.40, 13.06, 16.75, 21.15 and 21.37±0.25 (°2θ), measured with a Cu—Kα irradiation (1.54060 Å).

Polymorphic form (I) can be obtained according to the procedure described in example 1 and 2 of European patent EP 888 289 B1.

However, in some other solvents usable for crystallization, lacosamide may crystallize as form (II), or as a mixture of form (I) and form (II). In a particular aspect, the present invention also provides a process for the manufacture of polymorphic form (I) of (R)-2-acetamido-N-benzyl-3-methoxypropionamide.

For example, polymorphic form (I) of (R)-2-acetamido-N-benzyl-3-methoxypropionamide may be obtained by:
(i) dissolving (R)-2-acetamido-N-benzyl-3-methoxypropionamide in a solvent, preferably in ethyl acetate;
(ii) seeding with pure polymorphic form (I) of (R)-2-acetamido-N-benzyl-3-methoxypropionamide;
(iii) maintaining the suspension at the seeding temperature, then gradually cooling down;
(iv) washing with a solvent, preferably ethyl acetate and drying.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

$^1$H NMR spectra were recorded on a Varianc 400 MHz and 300 MHz spectrometer in deuteried solvents (CD$_3$OD, CDCL₃ or DMSO-d6 as appropriate) at room temperature. Chemical shifts are expressed in parts per million (ppm, δ) using tetramethylsilane as internal standard. Data were reported in the order of chemical shift, multiplicity (s, singlet; d, doublet; t, triplet; q, quartet; m, multiplet; app, apparent and/or multiple resonance), coupling constant (J) in hertz (Hz) and number of protons.

High Performance Liquid Chromatography (HPLC) chromatograms were recorded on different systems: Waters 2695 PDA (compounds F and D'''1), Agilent 1100 UV (compounds A1 and D3), Shimadzu-SCL-IOAVP (compounds G and D1). The column used was an lnertsil silica 5 microns (250×4.6 mm), the detection was performed at 240 nm and the mobile phase was n-hexane:ethanol:DEA (70:30:0.1). Sample concentration was 1 mg/ml for an injection volume of 10.0 μl, the flow was 1.0 ml per minute and the run time was 30 minutes. The HPLC data were reported in area %.

Gas chromatography (GC) was performed on Agilent-7890A series and Shimadzu-GC-17A. The column used was aDB-624, 30 m, 0.53 mm, 3.0 μm or equivalent. The injector temperature was 180° C., the FID detector temperature was 260° C. and the temperature program was 60° C. for 5> minutes, then a ramp of 10° C./minute up to 220° C., then an hold at 220° C. for 15 minutes. Sample concentration was 40 mg/ml (methanol as diluent) for an injection volume of 1.0 μl, the flow was 4.0 ml per minute and the split ration was 1:2. Carrier gas was nitrogen for a run time was 36.0 minutes. The GC data were reported in area %

Mass spectra were recorded on Waters 3100 triple quadrapole spectrometer.

Example 1

Preparation of (Z)-2-acetamido-N-benzyl-3-methoxyacrylamide (A1)

1a. Preparation of N-acetamido ethanoic acid (G)

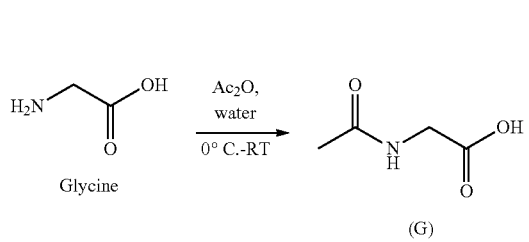

To a solution of glycine (100 g, 1.3 mol) in water (300 ml, 3 vol), acetic anhydride (252 ml, 2.6 mol) was added at 5° C. Allowed to room temperature, the reaction mixture was stirred for overnight. The reaction mixture was then cooled to 5° C., stirred for 1 h, filtered and the wet cake obtained was washed with cold water (200 ml) to afford a white colored solid compound. The obtained compound was dried under vacuum till constant weight was observed. Yield: 123 g; 80%.

¹H-NMR (300 MHz), (CD₃OH), δ 4.92 (bs, 1H, OH), 3.91 (s, 2H, CH2), 2.00 (s, 3H, CH3CO).

ESMS (m/e): 115.93 (M−1, 100) and 117.95 (M+1, 91)

1b. Preparation of 4-[(dimethylamino)methylene]-2-methyl-5(4H)-oxazolone

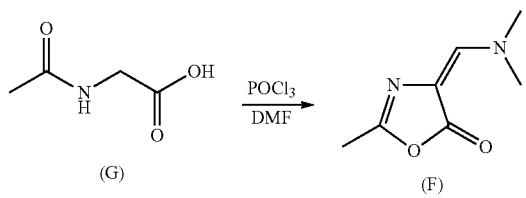

To a solution of (G) (200 g, 1.7 mol) in phosphorus oxy chloride (398.2 ml, 4.2 mol), dimethyl formamide (330 ml, 4.2 mol) was added slowly at 0-5° C. The reaction mixture was then allowed to room temperature, heated to 45° C. and stirred for 2 h. The reaction mixture was evaporated at 60° C. for 1 h on rotavapor then quenched with an aqueous NH₃ solution (2 L, 10 vol) at −10 to 10° C. and stirred at 0° C. for 1 h. The reaction mass was filtered to afford a brown colored compound. This solid was dissolved in CH₂Cl₂ (2 L) & water (500 ml), stirred for 10 min, filtered to remove undissolved particles. Separated layers and organic layer was washed with water (500 ml). The organic layer was dried over Na₂SO₄ and evaporated the solvent completely under reduced pressure to afford the brown colored solid compound. Yield: 195 g, 74% of (F).

¹H-NMR (300 MHz), (CDCl₃), δ 6.95 (s, 1H, =CH), 3.48 (s, 3H, NCH3), 3.19 (s, 3H, NCH3), 2.20 (s, 3H, =CCH3).

ESMS (m/e): 155.07 (M+1, 100) and 156.09 (M+2, 29)

1c. Preparation of 4-(hydroxymethylene)-2-methyl-5 (4H)-oxazolone, sodium salt (E)

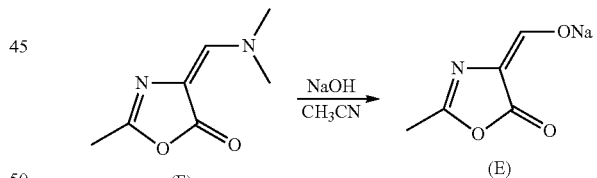

To a solution of (F) (200 g, 1.29 mol) in acetonitrile (1 L, 5 vol), 2N aqueous NaOH solution (62.3 g in 775 ml water; 1.55 mol) was added at 15-20° C., then allowed to room temperature and stirred overnight. Solvent mixture was evaporated completely to afford pale brown colored solid compound. Acetone (1 L) was added to the solid material and stirred for 30 min, filtered to get pure pale brown colored solid compound. Compound was dried under vacuum at 50° C., till constant weight was observed. Yield of (E): 155 g; 80%.

¹H-NMR (300 MHz), (DMSO-d6) δ 8.67 (s, 1H, =CHONa), 1.99 (s, 3H, =CCH3)

ESMS (m/e): 125.82 (M−1, 100)

1d. Preparation of (Z)-2-acetylamino-3-methoxy-2-propenoic acid, methyl ester (D2)

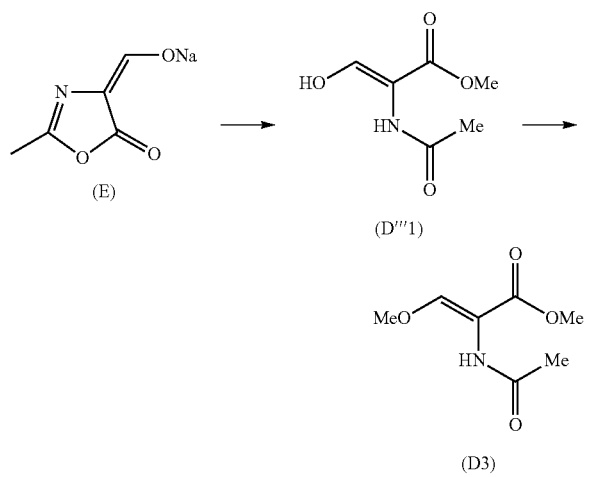

To a solution of (E) (70 g, 0.46 mol) in methanol (350 ml, 5 vol), 12% methanolic HCl (214 ml, 0.7 mol) was added at 0° C. and the stirring continued for 4 h at same temperature. Solvent was evaporated, the resulting crude (D'''1) was diluted with acetone (350 ml) and the slurry was filtered. To this acetone filtrate, $K_2CO_3$ (97.4 g, 0.7 mol) was added at 0° C. After 30 min, dimethylsulfate (DMS) (68.37 ml, 0.7 mol) was added slowly at 0° C. and continued the stirring for 6 h. The reaction mixture was allowed to room temperature, filtered and the filtrate was concentrated in vacuo to provide light yellowish crude liquid. On overnight storage solid was observed. Solid was stirred in toluene (140 ml) for 1 h, filtered, washed with toluene (70 ml) to afford pale yellow colored solid material Yield of (D3) 45.0 g; 55%.

ESMS (m/z) 174 (M+1), $^1$H-NMR (300 MHz), $(CD_3)_2SO$, δ, 8.8 (s, 1H, —NH), 7.25 (s, 1H, =CH), 3.8 (s, 3H, $COOCH_3$), 3.6 (s, 3H, —$OCH_3$), 1.8 (s, 3H, $COCH_3$)

1e. Preparation of (Z)-2-acetylamino-3-methoxy-2-propenoic acid (D1)

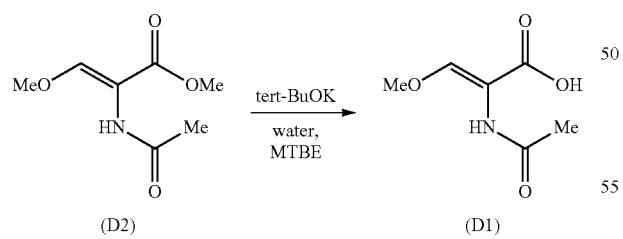

To a solution of potassium tert-butyl oxide (14.24 g, 0.127 mol) in tert-butyl methyl ether solvent (150 ml, 15 vol), water (1.14 ml, 0.063 mol) was added at 0° C. After 5 min, (D3) (10 g, 0.057 mol) was added lot wise at 0° C., allowed to room temperature and stirred for 5 h at same temperature. Reaction mixture was acidified with methanolic HCl till the pH attains ~2 at 0° C. and filtered to remove salts. Solvent was evaporated under reduced pressure to afford gummy crude material. Isopropylalcohol (20 ml) was added to this crude, stirred for 30 min, filtered, washed with Isopropylalcohol (10 ml) to afford off-white colored solid compound. 1$^{st}$ crop: 3.25 g (35%); Mother liquor was evaporated and purified by column chromatography (5% methanol in $CH_2Cl_2$), to afford (D1) as a white colored solid 1.6 g. (17%).

ESMS (m/z): 159.9 (M+1), 157.9 (M−1).
$^1$H NMR (300 MHz), $(CD_3)_2SO$, δ, 12 (s, 1H, —COOH), 8.6 (s, 1H, —NH), 7.15 (s, 1H, =CH), 3.6 (s, 3H, —$OCH_3$), 1.8 (s, 3H, $COCH_3$).

1f. Preparation of (Z)-2-acetylamino-N-benzyl-3-methoxypropenamide (A1)

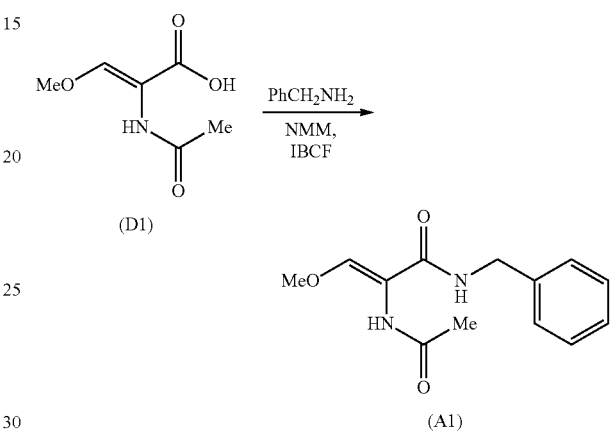

To a solution of (D1) (20 g, 0.125 mol) in $CH_2Cl_2$ (300 ml, 15 vol) and tetrahydrofuran (THF) (100 ml, 5 vol), N-methylmorpholine (NMM) (16.6 ml, 0.15 mol) was added slowly at −40° C. After 20 min, isobutylchloroformate (IBCF) (19.67 ml, 0.15 mol) was added at same temperature and stirred for 20 min. Benzylamine (16.5 ml, 0.15 mol) in tetrahydrofuran (40 ml) was added at −40° C., then the reaction mixture was stirred for 1 h and allowed to room temperature. Solvent was evaporated under reduced pressure. The obtained crude was purified by column chromatography in 5% methanol in chloroform to afford (A1) as a white colored powder. Yield: 17 g; 55%.

ESMS m/z value 249 (M+1), $^1$H-NMR (300 MHz), $(CD_3)_2SO$, δ, 8.6 (s, 1H, —NH), 8.0 (s, 1H, —CONH—), 7.3 (m, 5H, aromatic), 7.15 (s, 1H, =CH), 4.3 (d, 2H, benzylic), 3.6 (s, 3H, —$OCH_3$), 1.8 (s, 3H, $COCH_3$).

Example 2

Preparation of Substantially Optically Pure (R)-2-acetamido-N-benzyl-3-methoxypropion-amide (B1) by Catalytic Asymmetric Hydrogenation of Compound of Formula (A1)

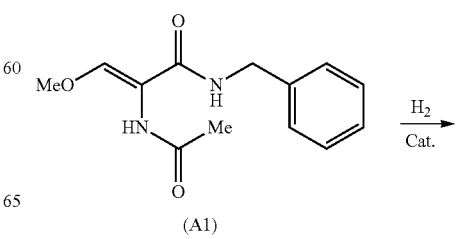

-continued

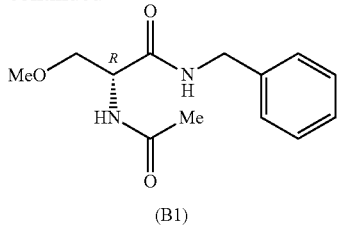

(B1)

Catalyst:
(S,S)-Ph-BPE-Rh: (−)-1,2-Bis((2S,5S)-2,5-diphenylphospholano)ethane(1,5-cyclooctadiene)rhodium(I) tetrafluoroborate.

Solvent:
methanol

Hydrogenation was carried out in a 10 Vessel Multicell Reactor (Baskerville®). The substrate Z-2-Acetamido-N-Benzyl-3-methoxyacrylamide (A1) (1 g) was placed in a glass reactor with a magnetic stirrer bar and then placed in the stainless steel high pressure vessel. Catalyst (1 mg, 0.1% w/w) and methanol (5 mL) were added. Substrate, catalyst and solvent were charged under a nitrogen atmosphere. The vessel was sealed and purged with hydrogen by pressurising the vessel to 10 barg and then releasing the pressure (2 times). Finally, the hydrogen pressure was adjusted to 10 barg and the reaction mixture was stirred at 45° C. for 20 hours. The reaction was stopped by purging the vessel with helium and the reaction mixture was analysed by chemical & chiral HPLC analysis.

Conversion measured by chemical HPLC showed 100% conversion of (A1).

Chiral HPLC showed that 99.8% of (B1) was obtained, hence an enantiomeric excess of 99.6%.

Example 3

Synthesis of N-acetyl-O-methyl-D-serine (C1)

Example 3a

By Catalytic Asymmetric Hydrogenation of Compound of Formula (D1)

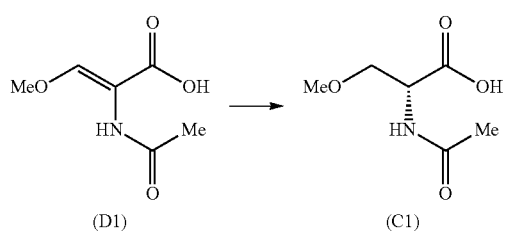 [SMILES: CO/C=C(\NC(C)=O)C(=O)O ; COC[C@@H](NC(C)=O)C(=O)O ; "(D1)" ; "(C1)"]

Catalyst:
(S,S)-Ph-BPE-Rh=(−)-1,2-Bis((2S,5S)-2,5-diphenylphospholano)ethane(1,5-cyclooctadiene)rhodium(I) tetrafluoroborate.

Hydrogenation was carried out in a 10 Vessel Multicell Reactor (Baskerville®). Substrate, catalysts and solvent were charged under a nitrogen atmosphere. The substrate Z-2-Acetamido-3-methoxyacryic acid (D1) (1 g) was placed in a glass reactor which with a magnetic stirrer bar was then placed in the stainless steel high pressure vessel. Catalyst (1 mg, 0.1% w/w) and methanol (5 mL) were added. The vessel was sealed and purged with hydrogen by pressurising the vessel to 10 barg and then releasing the pressure (2 times). Finally, the hydrogen pressure was adjusted to 10 barg and the reaction mixture was stirred at 45° C. for 20 hours. The reaction was stopped by purging the vessel with helium and the reaction mixture was analysed by chemical & chiral HPLC analysis.

Conversion measured by chemical HPLC showed 100% conversion of (D1) with 98.6% chemical purity.

Chiral HPLC showed that 99.8% of N-acetyl-o-methyl-D-serine (C1) was obtained, hence an enatiomeric excess of 99.6%.

Example 3b

By hydrolysis of Compound of Formula (C2)

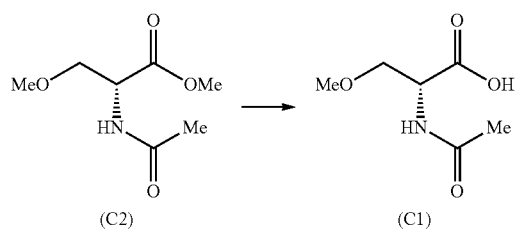 [SMILES: COC[C@@H](NC(C)=O)C(=O)OC ; COC[C@@H](NC(C)=O)C(=O)O ; "(C2)" ; "(C1)"]

Prepared by adapting the procedure described in Tetrahedron: Asymmetry, 9, 3841 (1998)

A saturated aqueous solution of sodium hydrogenocarbonate containing (C2) was stirred at room temperature for 24 h. The solution was extracted with diethylether and the aqueous layer was acidified to pH 3.0 with 5N HCl. The acidic solution was evaporated to dryness and the residue suspended in dichloromethane. The insoluble salts were removed by filtration and washed with dichloromethane. The dichloromethane layers were combined and evaporated in vacuo to afford N-acetyl-o-methyl-D-serine (C1) as an off-white foam.

Example 4

Preparation of methyl(R)-2-acetamido-3-methoxypropionate (C2) by catalytic asymmetric hydrogenation of (Z)-methyl-2-acetamido-3-methoxypropenoate (D2)

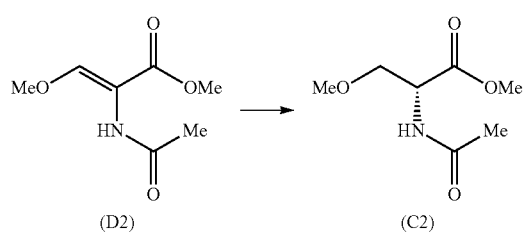 [SMILES: CO/C=C(\NC(C)=O)C(=O)OC ; COC[C@@H](NC(C)=O)C(=O)OC ; "(D2)" ; "(C2)"]

Catalyst:
(R—R)—Rh-DIPAMP(COD)BF$_4$=(R,R)-(−)-1,2-Bis[(o-methoxyphenyl)(phenyl) phosphino]ethane(1,5-cyclooctadiene)rhodium(I) tetrafluoroborate.

Hydrogenation was carried out in a 10 Vessel Multicell Reactor (Baskerville®). Substrate, catalysts and solvent were charged under a nitrogen atmosphere. The substrate (Z)-methyl-2-acetamido-3-methoxyacrylate (350 mg) was placed in a glass reactor which with a magnetic stirrer bar was then placed in the stainless steel high pressure vessel. A catalyst solution (3.5 mg in 10 mL of methanol) is prepared. 1 mL of the catalyst solution and methanol (4 mL) were added to the glass reactor. The vessel was sealed and purged with hydrogen by pressurising the vessel to 5 barg and then releasing the pressure (2 times). Finally, the hydrogen pressure was adjusted to 10 barg and the reaction mixture was stirred at 45° C. for 20 hours. The reaction was stopped by purging the vessel with helium and the reaction mixture was analysed by chiral HPLC analysis.

Chemical HPLC showed 100% conversion of (D2) with 97% chemical purity.

Chiral HPLC showed that 97% of (C2) was obtained, hence an enatiomeric excess of 94%.

Example 5

Preparation of substantially optically pure (R)-2-acetamido-N-benzyl-3-methoxypropion-amide (B1) from N-acetyl-O-methyl-D-serine (C1)

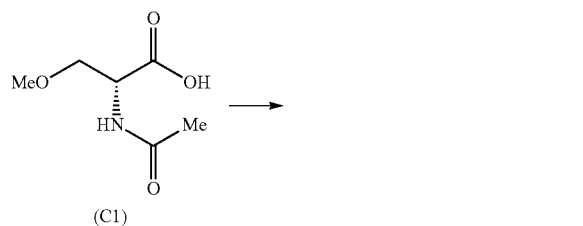

To a solution of (C1) in tetrahydrofuran (10 volumes) cooled at −10° C. was added dropwise over 10 minutes 1.0 equiv of isobutylchloroformate. After 10 minutes, 1.0 equiv of N-methylmorpholine was added dropwise over 10 minutes and the suspension stirred at −10° C. for 40 minutes. 1 Equiv of benzylamine was then added over 10 minutes and the suspension stirred for 10 minutes. The reaction was quenched at −10° C. by addition of 1N HCl (0.6 equiv) to pH 0-1. The reaction was transferred to a separatory funnel and diluted with 20 volumes of dichloromethane. The layers were separated and the aqueous layer extracted again with 20 volumes of dichloromethane. The combined organic layers were washed with a 5% solution of sodium bicarbonate and evaporated to dryness.

The crude (B1) was suspended in ethyl acetate (10 volumes), heated to reflux, seeded with form (I) of (R)-2-acetamido-N-benzyl-3-methoxypropion-amide and slowly cooled down to room temperature to afford substantially optically pure (R)-2-acetamido-N-benzyl-3-methoxypropion-amide (B1) in crystalline form (I).

(R)-2-acetamido-N-benzyl-3-methoxypropion-amide obtained according to this example is characterized by a powder X-ray diffractogram (FIG. 1) comprising peaks at 8.40, 10.52, 13.06, 15.72, 16.75, 17.8, 19.68, 21.15, 21.37, 24.37, 25.04 and 25.49±0.25 (°2θ), measured with a Cu—Kα irradiation.

The invention claimed is:

1. A compound of general formula (A),

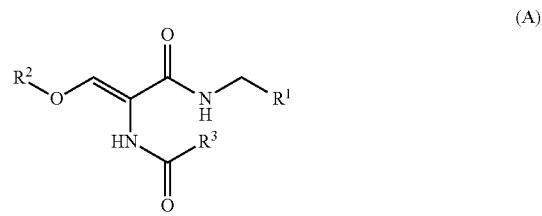

wherein

R$^1$ is an aryl; and

R$^2$ and R$^3$ are independently a substituted or unsubstituted alkyl.

2. The compound of general formula (A) according to claim 1 wherein R$^1$ is a phenyl and R$^2$ and R$^3$ are independently methyl.

3. The compound of formula (A) according to claim 1 which is (Z)-2-acetamido-N-benzyl-3-methoxyacrylamide (A1).

4. A process of manufacturing a compound of formula (A), which process comprises reacting a compound of general formula (D') with a compound of formula R$^1$CH$_2$NH$_2$ in a solvent in the presence of a base,

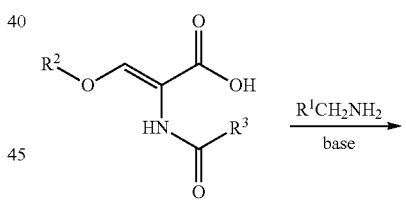

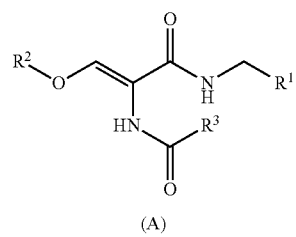

wherein

R$^1$ is aryl, and

R$^2$ and R$^3$ are independently a substituted or unsubstituted alkyl.

5. A process of manufacturing a compound of formula (B) having at least 95% optical purity, which process comprises conducting catalytic asymmetric hydrogenation of a compound of general formula (A),

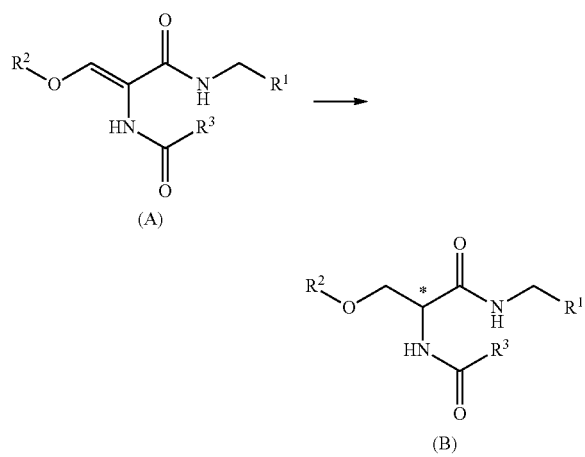

(A)

(B)

wherein
R¹ is aryl, and
R² and R³ are independently a substituted or unsubstituted alkyl.

6. The process according to claim 5 which is performed in the presence of a chiral catalyst selected from the group consisting of 1,2-Bis((2R,5R)-2,5-dimethylphospholano)benzene(1,5-cyclooctadiene)rhodium(I) tetrafluoroborate; (+)-1,2-Bis((2S,5S)-2,5-diphenylphospholano)ethane(1,5-cyclooctadiene)rhodium(I) tetrafluoroborate; (−)-1,2-Bis((2S,5S)-2,5-dimethylphospholano)ethane(1,5-cyclooctadiene)rhodium(I) tetrafluoroborate; (1S,2S)-Bis(2-methoxyphenyl)phenylphosphino)ethane(1,5-cyclooctadiene)rhodium(I) tetrafluoroborate; (1S,1'S,2R,2'R)-1,1'-Di-t-butyl-[2,2']-diphospholane (1,5-cyclooctadiene)rhodium(I) tetrafluoroborate; (R)-(+)-(2,2'-Bis(diphenylphosphino)-1,1'-binaphthyl)ruthenium; (−)-2,3-Bis[(2R,5R)-2,5-dimethylphospholanyl]-1-methyl-1H-pyrrole-2,5-dione(1,5-cyclooctadiene)rhodium(I) tetrafluoroborate; (1R,1R',2S,2S')-(+)-2,2'-Di-t-butyl-2,3,2',3'-tetrahydro-1,1'-bi-1H-isophosphindole(1,5-cyclooctadiene)rhodium(I) tetrafluoroborate; (R)-(−)-1,13-Bis(diphenylphosphino)-7,8-dihydro-6H-dibenzo[f,h][1,5]dioxonin (1,5-cyclooctadiene)rhodium(I) tetrafluoroborate; (R,R)-(−)-1,2-Bis[(R)-4,5-dihydro-3H-binaphtho[1,2-c:2',1'-e]phosphepino]benzene(1,5-cyclooctadiene)rhodium(I) tetrafluoroborate; (−)-1,2-Bis((2R,5R)-2,5-diethylphospholano)benzene(1,5-cyclooctadiene)rhodium(I) tetrafluoroborate.

7. The process according to claim 5 which is performed in a solvent selected from the group consisting of methanol, tetrahydrofuran, ethanol and 2-methyl-tetrahydrofuran.

8. The process according to claim 5 which is performed at a temperature comprised between about 20° C. and about 45° C.

9. The process according to claim 5 which is performed under a pressure of hydrogen comprised between about 5 Barg and about 10 Barg.

10. The process according to claim 5 wherein the ratio substrate/catalyst expressed in Mol % is at least about 1000.

11. A process of manufacturing (R)-2-acetamido-N-benzyl-3-methoxypropion-amide (B1) having at least 95% optical purity comprising conducting catalytic asymmetric hydrogenation of (Z)-2-acetamido-N-benzyl-3-methoxyacrylamide (A1), in the presence of hydrogen using a chiral catalyst

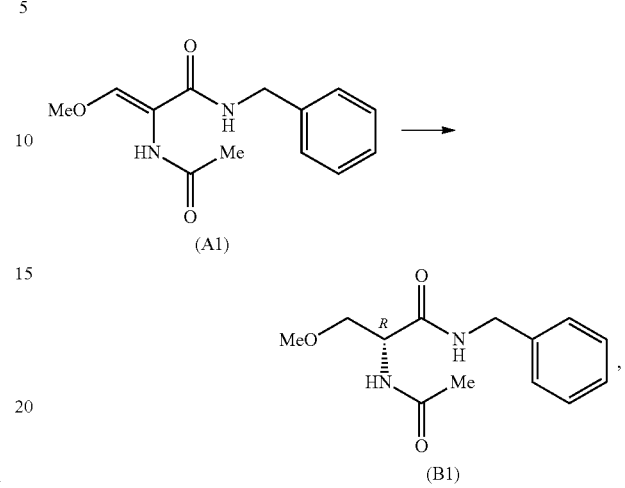

wherein the chiral catalyst is selected from the group consisting of 1,2-Bis((2R,5R)-2,5-dimethylphospholano)benzene (1,5-cyclooctadiene)rhodium(I) tetrafluoroborate, (+)-1,2-Bis((2S,5S)-2,5-diphenylphospholano)ethane(1,5-cyclooctadiene)rhodium(I) tetrafluoroborate and (−)-1,2-Bis((2S,5S)-2,5-dimethylphospholano)ethane(1,5-cyclooctadiene)rhodium(I) tetrafluoroborate.

12. The process according to claim 11, comprising, hydrolyzing (Z)-methyl-2-acetamido-3-methoxypropenoate (D2), into Z-2-Acetamido-3-methoxyacryic acid (D1),

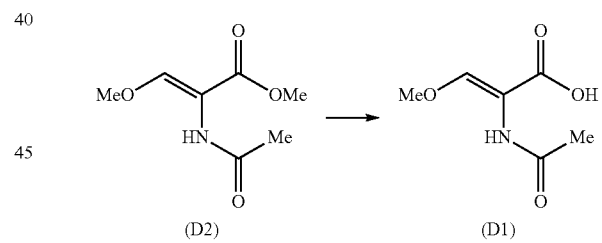

(ii) reacting 2-Acetamido-3-methoxyacryic acid (D1) obtained in step (i) with benzylamine in the presence of ethylchloroformiate (ECF) or isobutylchloroformiate (IBCF) and a base to afford (Z)-2-acetamido-N-benzyl-3-methoxyacrylamide (A1),

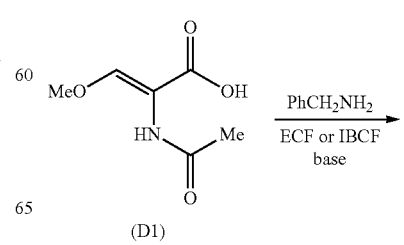

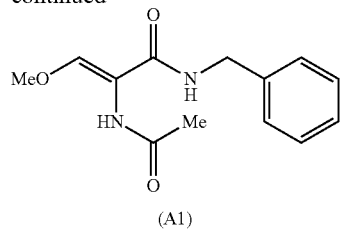

(iii) performing catalytic asymmetric hydrogenation of (Z)-2-acetamido-N-benzyl-3-methoxyacrylamide (A1) obtained in step (ii), in the presence of a chiral catalyst

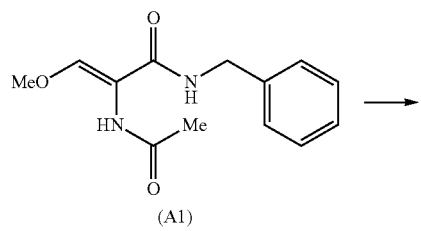

wherein the chiral catalyst is selected from the group consisting of 1,2-Bis((2R,5R)-2,5-dimethylphospholano)benzene(1,5-cyclooctadiene)rhodium(I) tetrafluoroborate, (+)-1,2-Bis((2S,5S)-2,5-diphenylphospholano)ethane(1,5-cyclooctadiene)rhodium(I) tetrafluoroborate and (−)-1,2-Bis((2S,5S)-2,5-dimethylphospholano)ethane(1,5-cyclooctadiene)rhodium(I) tetrafluoroborate.

13. A process of manufacturing (R)-2-acetamido-N-benzyl-3-methoxypropion-amide (B1) having at least 95% optical purity consisting essentially of, (i) conducting catalytic asymmetric hydrogenation of 2-acetamido-3-methoxyacrylic acid (D1),

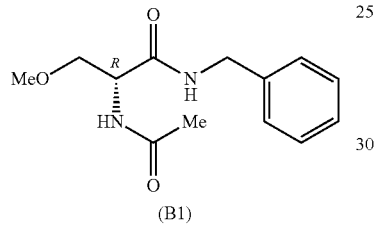

(ii) reacting N-acetyl-O-methyl-D-serine (C1) obtained in (i) with benzylamine in THF or dichloromethane in the presence of ethyl chloroformate or isobutylchloroformate as activating agent and N-methylmorpholine as base,

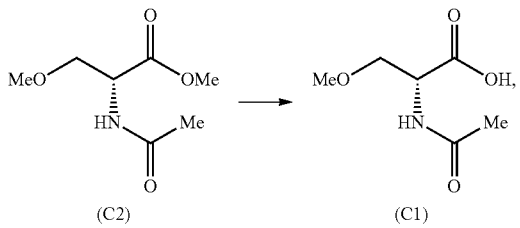 [SMILES: COC[C@@H](NC(C)=O)C(=O)OC ; COC[C@@H](NC(C)=O)C(=O)O ; "(C2)" ; "(C1)"]

14. A process of manufacturing (R)-2-acetamido-N-benzyl-3-methoxypropion-amide (B1) having at least 95% optical purity comprising (i) hydrolyzing methyl(R)-2-acetamido-3-methoxypropionate (C2),

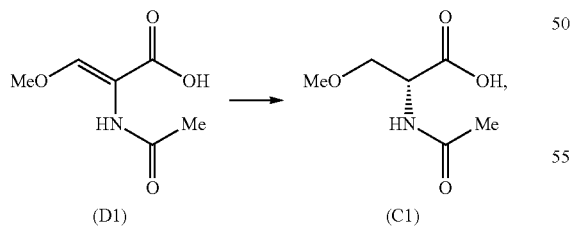

(ii) reacting N-acetyl-O-methyl-D-serine (C1) obtained f(i), with benzylamine in THF or dichloromethane in the presence of ethyl chloroformate or isobutylchloroformate as activating agent and N-methylmorpholine as base.

* * * * *